United States Patent [19]

Cohen

[11] Patent Number: 4,539,049

[45] Date of Patent: Sep. 3, 1985

[54] ALUMINUM ZIRCONIUM METALLO-ORGANIC COMPLEX USEFUL AS COUPLING AND HYDROPHOBIC AGENTS

[75] Inventor: Lawrence B. Cohen, Sharon, Mass.

[73] Assignee: Jos. Cavedon Co., Inc., Woonsocket, R.I.

[21] Appl. No.: 478,043

[22] Filed: Mar. 22, 1983

Related U.S. Application Data

[63] Continuation-in-part of Ser. No. 465,207, Feb. 9, 1983.

[51] Int. Cl.$^3$ .................................................. C07F 7/00
[52] U.S. Cl. ........................... 106/287.17; 106/287.19; 556/27
[58] Field of Search ............................ 260/429.3, 414; 428/411, 432, 446, 537, 699; 106/287.17, 287.19

[56] References Cited

U.S. PATENT DOCUMENTS

| | | |
|---|---|---|
| 2,832,754 | 4/1958 | Jex et al. . |
| 2,930,809 | 3/1960 | Jex et al. . |
| 2,941,918 | 6/1960 | West . |
| 2,946,701 | 7/1960 | Plueddemann . |
| 3,030,320 | 4/1962 | Haslam . |
| 3,032,570 | 5/1962 | Haslam . |
| 3,044,982 | 7/1962 | Jex et al. . |
| 3,045,036 | 7/1962 | Jex et al. . |
| 3,334,119 | 8/1967 | Cohen . |
| 3,405,153 | 10/1968 | Jones et al. ........................ 260/429.3 |
| 3,419,587 | 12/1968 | Harson ......................... 260/429.3 X |
| 3,553,316 | 1/1971 | Rubino ......................... 260/429.3 X |
| 3,660,134 | 5/1972 | Morris et al. . |
| 3,697,474 | 10/1972 | Morris et al. . |
| 3,697,475 | 10/1972 | Morris et al. . |
| 3,792,068 | 2/1974 | Luedders et al. ................ 260/429.3 |
| 3,981,986 | 9/1976 | Rubino ............................ 260/429.3 |
| 4,017,599 | 4/1977 | Rubino ........................ 260/429.3 X |
| 4,080,353 | 3/1978 | Monte et al. . |
| 4,102,642 | 7/1978 | Banks . |
| 4,141,751 | 2/1979 | Moreland . |
| 4,152,311 | 5/1979 | Monte et al. . |
| 4,223,010 | 9/1980 | Rubino et al. ............... 260/429.3 X |
| 4,360,544 | 11/1982 | Franz et al. .................... 428/432 X |
| 4,414,275 | 11/1983 | Woods ........................... 428/411 X |

OTHER PUBLICATIONS

D. N. Solomon et al., "Chemistry of Pigments and Fillers", 108–178, (John Wiley and Sons, 1983).

*Primary Examiner*—Helen M. S. Sneed
*Attorney, Agent, or Firm*—David G. Conlin; Ernest V. Linek

[57] ABSTRACT

This invention relates to novel compositions of matter which are mixed metal metallo-organic complex agents comprised of a chemically united complex aluminum moiety and a tetravalent zirconium moiety. The specific process for preparing such compositions in organic/solvent media with desirable hydrolytic stability is described.

Further described are compositions of matter wherein the aforementioned metallo-organics are employed to chemically modify the surface of fibrous and particulate inorganic substances and certain organic particulates, thereby resulting in hydrophobic, organophilic fibers and particles having improved rheological properties which facilitate higher filler (fiber) loading levels and serve to enhance the physical properties of composite articles and coatings formed therewith.

24 Claims, 7 Drawing Figures

ALUMINUM ZIRCONIUM METALLO-ORGANIC COMPLEX USEFUL AS COUPLING AND HYDROPHOBIC AGENTS

BACKGROUND OF THE INVENTION

This application is a continuation-in-part of U.S. application Ser. No. 465,207, filed Feb. 9, 1983, the disclosure of which is incorporated herein by reference.

This invention relates to the manufacture of composite products, such products to be defined as containing chemically dissimilar materials most generally typified by an organic nonpolar substance and an inorganic polar substance. Specifically, the invention describes the preparation and use of novel mixed metal metallo-organic substances which are useful in chemically modifying the particulate or fibrous materials, preferably inorganic materials, for incorporation into the resin matrices with which they will share an interfacial boundary.

It is recognized by those skilled in the art that manufacture of mineral filled or fiber reinforced plastic or rubber articles offers unique problems associated with the poor wetting of the mineral or fiber by the resin. Subsequently, interfacial failure can occur and is augmented in most applications by the presence of moisture which migrates to the interface in the absence of any surface treatment of the mineral filler or fiber and will result in substantial loss in flexural and tensile strength properties. An identical problem is observed in analogous composite systems such as paints and coatings, paper, adhesives, sealants and other compositions containing the organic/inorganic interface.

Historically, fibers, most specifically fiber glass, have been treated with methacrylate chromic chloride as disclosed in: U.S. Pat. Nos. 2,273,040; 2,524,803; 2,552,910; 2,544,666; 2,554,667; 2,544,668; 2,611,718; and trialkoxy silanes as disclosed in: U.S. Pat Nos. 2,742,378; 2,776,910; 2,832,754; 2,930,809; 2,946,701; 3,045,036; 3,169,884; 3,211,684; 3,258,477; 3,849,471.

Both of these materials impart additional dry and wet strength properties to glass reinforced fabricated articles. Silanes have also enjoyed usage as a preferred surface treatment for mineral fillers such as silica, alumina trihydrate, mica, wollastonite, and glass beads when such are to be used in applications wherein physical strength of the composite is an important performance property. More recently, organo titanates, such as described in U.S. Pat. Nos. 4,096,110; 4,098,758; 4,141,751; and 4,152,311 have found some application in mineral filler thermoplastic composites. In other less demanding applications as are found in paper manufacture and some coating areas it is viable to use surfactants or fatty acid salts to chemically alter the inorganic substrate.

The usefulness of silanes is offset by their high cost, requirement for heat input to react with fillers, and handling problems related to rapid hydrolysis and polymerization in the presence of moisture which greatly reduces their effectiveness. Titanates are also hindered by undesirable economics, albeit not as severe as silanes, and also by their limited application in aqueous environments and in products wherein strength properties are significant.

The compositions to be described herein are unique substances which are highly soluble in water and a variety of polar organics, hydrolytically stable, cost effective viz-a'-viz aforementioned silanes and titanates, and highly reactive, reacting essentially instantaneously with mineral fillers and functional organic particulates at ambient temperature. The said compositions are predicated upon an important symbiotic relationship which recognizes the preferred reactivity of inorganic substrates with the aluminum portion of the molecule and the predictable advantages of using a tetravalent transition metal for purposes of complexation with a reactive organic.

SUMMARY OF THE INVENTION

Figure 1:
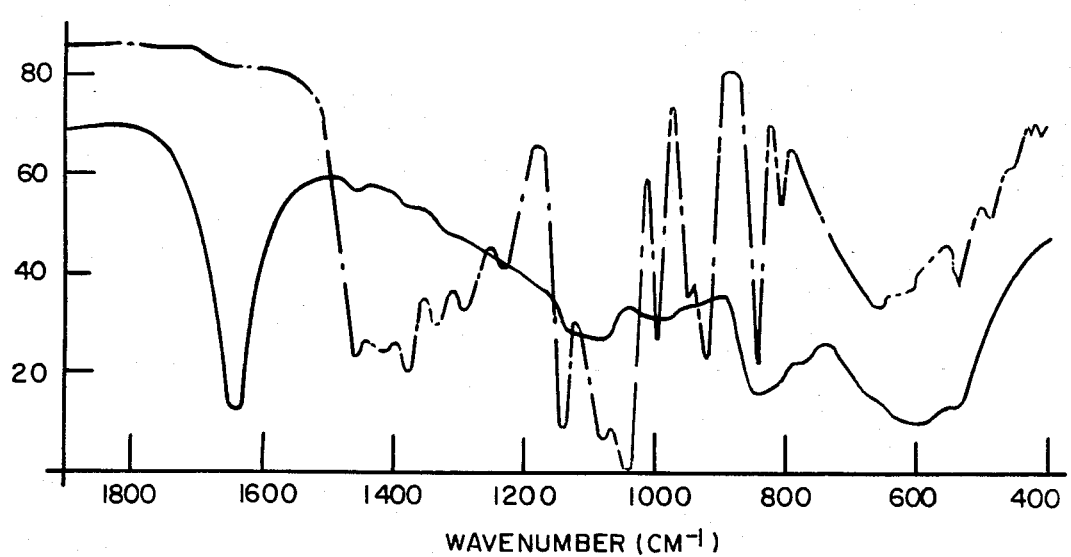
FIG. 1 is a reproduction of an infra red (IR) spectroscopy scan comparing the curves obtained from scanning unreacted propylene glycol (dotted lines) with sec-propanolato aluminum chlorhydrate (solid line).
Figure 2:
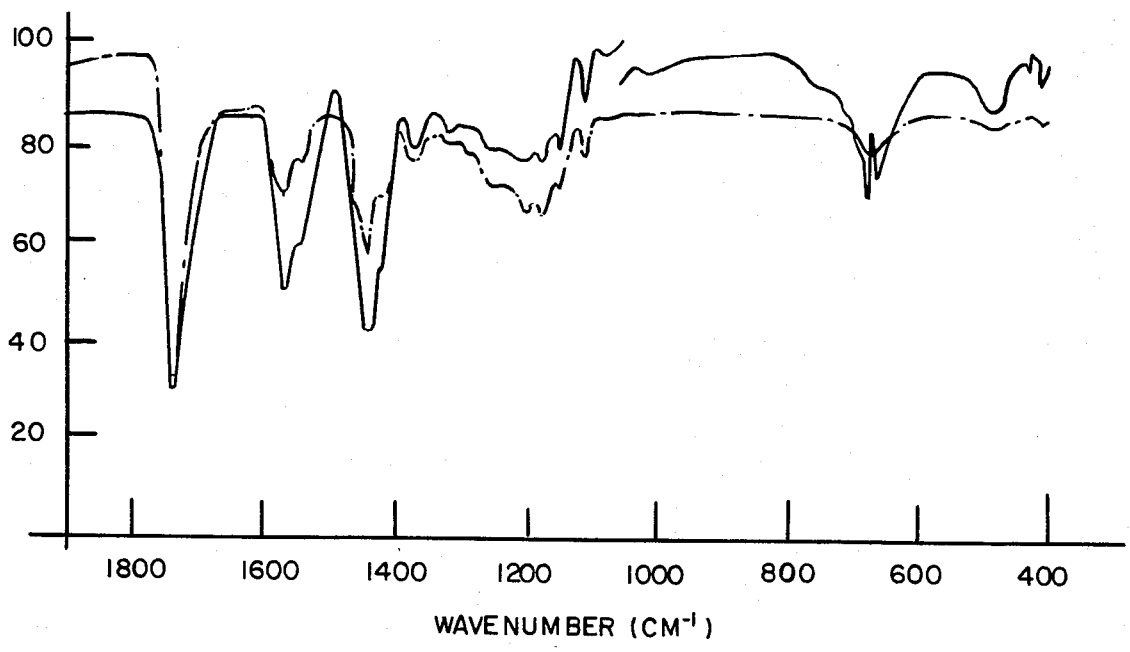
FIG. 2 is the IR scan for the reaction products of adipic acid and zirconium oxychloride (two phase).
Figure 3:
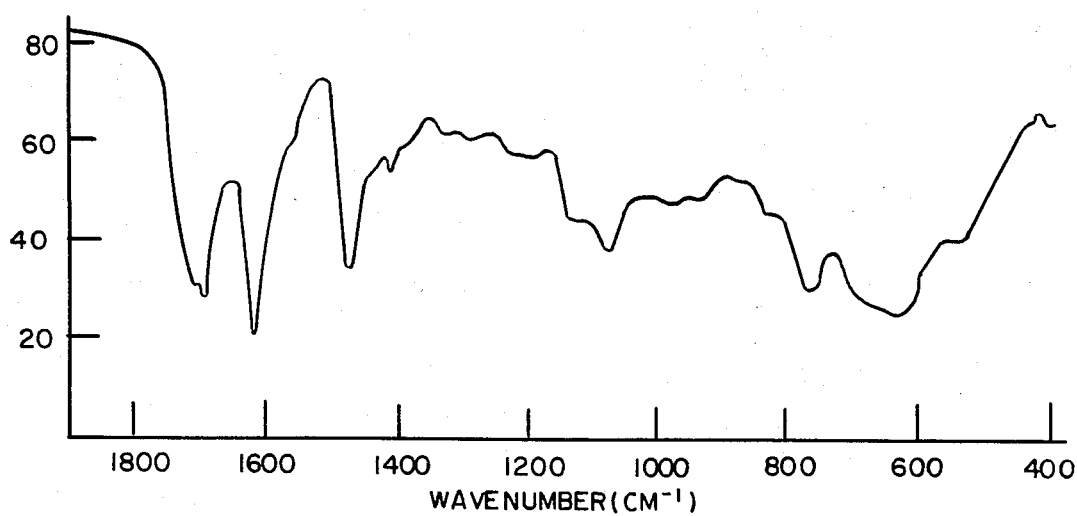
FIG. 3 is the IR scan of the reaction product of adipic acid and complexed aluminum chlorohydrate.

The subject invention pertains to compositions of matter which are the complex reaction products of (I) chelate-stabilized aluminum compositions, (preferably chelate stabilized aluminum chlorhydrates), (II) zirconium oxyhalide (preferably oxychloride), and (III) carboxylic acids. The reactants utilized to obtain the compositions of the present invention can generally be represented by the empirical formulas (I), (II), and (III):

$$Al_2(R_1O)_a A_b B_c \qquad (I)$$

$$ZrA_d B_e \qquad (II)$$

$$\begin{array}{c} R_2 \\ | \\ HO-C=O \end{array} \qquad (III)$$

wherein: A and B may be halogen, most preferably chlorine, hydroxy. Preferably A and B are chloro or hydroxy, a is a numerical value ranging from about 0.05 to 2, preferably 0.1 to 1, b is a number ranging from about 0.05 to 5.5, preferably about 1 to 5; and c is a number ranging from 0.05 to 5.5, preferably about 1 to 5, provided that $2a+b+c=6$ in the chelate stabilized aluminum reactant. Most preferably A is hydroxy and b ranges from 2 to 5, and B is chlorine and ranges from 1 to 3.8. The variables d and e have a numerical value from 0.05 to 4, provided that $d+e=4$ in the zirconium oxyhalide metallo-organic complex reactant. Preferably there is at least one hydroxy group and one halogen group in he zirconium reactant. More preferably the empirical ratio of hydroxy to the zirconium in this group is from about 1-2, and the ratio of halogen to zirconium is about 2-3, in that reactant.

In the aluminum containing segment of Formula I, pairs of aluminum atoms are joined by bidentate chelating ligands wherein:

(1) —OR₁O— is an alpha, beta or alpha, gamma glycol in which R₁ is an alkyl, alkenyl, alkynyl, or aralkyl group having from 1 to 6 carbon atoms, most preferably 2 to 3 carbon atoms, such ligands to be used exclusively or in combinations within a given composition, or (2) —OR₁O— is an alpha-hydroxy carboxylic acid

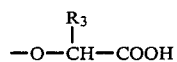

having from 2 to 6 carbon atoms, preferably 2 to 3 carbon atoms (i.e. preferably R₃ is H or CH₃).

In each instance the organic ligand is bound to two aluminum atoms through two oxygen heteroatoms.

The organofunctional ligand —(OC(R₂)O— is a moiety which can be derived from one of, or a combination of, the following groups:

(1) An alkyl, alkenyl, alkynyl, aryl or aralkyl carboxylic acid having from 2 to 36 carbon atoms, the preferred range being 4 to 18 carbon atoms;

(2) an aminofunctional carboxylic acid having from 2 to 36 carbon atoms, the preferred range being 4 to 18 carbon atoms;

(3) a dibasic carboxylic acid having from 2 to 18 carbon atoms wherein both carboxy groups are preferably terminal, the preferred range being 2 to 6 carbon atoms, or;

(4) acid anhydrides of dibasic acids having from 2 to 18 carbon atoms, the preferred range being 2 to 6 carbon atoms;

(5) a mercapto functional carboxylic acid having from 2 to 18 carbon atoms, the preferred range being 2 to 6 carbon atoms;

(6) an epoxy functional carboxylic acid having from 2 to 18 carbon atoms, preferably from 2 to 6 carbon atoms.

An extensive variety of —OC(R₂)O— anionic ligands is useful in the preparation of the subject compositions. Examples of specific dibasic acids include the anions of oxalic, malonic, succinic, glutonic, adipic, tartaric, itaconic, maleic, fumaric, phthalic and terephthalic. Example of fatty acides, include myristic, palmitic, stearic, oleic, linoleic and linolenic acids. In some compositions, in accordance with the present invention, the hydrophobicity imparted by the fatty acids provides a preferred material.

Examples of specific aminofunctional carboxylate anions, —OC(R₂)O— include the anions of glycine, alanine, beta-alanine, valine, leucine, isoleucine, phenylalanine, tyrosine, serine, threonine, methionine, cysteine, cystine, proline, hydroxyproline, aspartic, and glutaric acids.

Examples of specific monobasic carboxylate anions, —OC(R₂)O— include the anions of acetic, propionic, butyric, pentanoic, hexanoic, heptanoic, octanoic, dodecanoic, myristic, palmitic, stearic, isostearic, propenoic, 2-methylpropenoic, butenoic, hexenoic, benzoic and cinnammic acids.

Examples of the anhydrides of dibasic acids include phthalic, isophthalic and terephthalic anhydrides.

Examples of chelating ligands (—OR₁O—) include: ethylene glycol, propylene glycol, glycerol, etc. Examples of alpha-hydroxy acids R₃'CH(OH)COO— are glycolic, lactic, alpha-hydroxybutyric, and tartaric acids and those known in the art.

While not wishing to be bound by theory, characterization of these compositions using infrared spectroscopy (FIGS. 1, 2, 3, 4) has indicated that greater than 99% (>70% where C₁₂-C₁₈ carboxylates are used) of the organofunctional ligand, —OC(R₂)O— is present in complex form (i.e. has reacted) in the aluminum zirconium metallo-organic, and furthermore, that the organofunctional ligands are bound to an aluminum metal center on the one hand and to a zirconium metal center on the other. The IR information also indicated that the chelating agent (—OR₁O—) forms a chelated complex with aluminum.

Thus, the reaction product apparently involves the chelated aluminum moiety bridged to the zirconium oxychloride moiety through the organofunctional ligand. This may be empirically represented by formula IV:

wherein A and B are as above-defined, and a, b, c, d and e are as above defined, except that, in order to form the bonds depicted, the substituents attached to the metal groups are appropriately reduced, i.e. 2a+b+c=4 (2a+b+c=5 when the aluminum moiety is a terminal group), and d+e=2 (d+e=3 when zirconium moiety is a terminal group). When the aluminum moiety or the zirconium moiety forms the terminus in the molecular chain, one of the A or B groups may be replaced by a lower alkoxy group having 1 to 6 carbon atoms.

X, Y and Z are at least each 1, and may vary from 1 to 100 or more, depending on the reactivity of the particular materials and the desired form of the product. The molar ratio of aluminum moiety to zirconium moiety (X to Z) may vary from about 1.5 to 10, with the preferred ratio being from about 3 to 6. The ratio of organofunctional ligand to total metal (Y/(2X+Z)) may vary from about 0.05 to 2.0, with the preferred ratio being about 0.1 to 1.0.

The composition cited herein is preferably not prepared in the absence of solvent to avoid encountering undesirable hydrolysis and polymerization reactions resulting in a highly polymeric solid reaction product.

Preparation of the subject composition is preferably attained in solvents which may be comprised of lower alcohols having 1 to 6 carbon atoms and lower ketones having 1 to 6 carbon atoms, wherein the water content may vary from 0% to 5%. The active matter of compositions so prepared is from 10%-60%, preferably from 15%-50%. Pursuant to such preparation the product may be spray dried, freeze dried or otherwise solvent stripped to leave a solid having high activity.

In the aforementioned U.S. application Ser. No. 465,207 filed Feb. 9, 1983, broad classes of aluminum zirconium metallo-organic complexes were described. It has also been discovered that such complex compositions, when prepared in substantially water free organic solvent systems, are soluble in various non-aqueous solvents, and have properties such as coupling agents which are particularly advantageous in systems adversely affected by the presence of water. Thus, those hydrophobic embodiments of the present invention can be used as coupling agents for inorganic pigments, fibers or fillers in polymer systems which cannot effectively tolerate water or moisture, including polyolefins, various elastomers, epoxies. etc., or in water free systems such as solvent based paints, adhesives, caulks, coatings, etc., as well as many plastic products and forms, such as films, extruded or molded forms, etc., which are found substantially in the absence of water. The metallo-organic complex thus prepared is substantially hydrophobic and is soluble in a wide variety of non-aqueous solvents. Suitable industrial solvents are well known, and include alcohols, ketones, carboxylic acids and their esters, tetrahydrofuran, dioxane, dimethylsulfone , dimethylformamide, dimethylacetamide, carbon tetrachloride, mineral oil, toluene, xylene and similar organic solvents.

The present invention also provides a process for preparing compositions described above. Hydrolytically stable products having a shelf life in excess of 30 days can be prepared by complexation of the dimeric aluminum chlorohydrate moiety with a bidentate chelating ligand which imparts hydrolytic stability, such as an alpha, beta or alpha, gamma glycol having from 1 to 6 carbon atoms, the preferred ligands having 2 to 3 carbon atoms; or with an alpha-hydroxy carboxylic acid having 2 to 6 carbon atoms. Such complexation should utilize a mole ratio of complexing ligand to dimeric Al of 0.05 to 2, the preferred ratio being 0.10 to 1.00. The stabilized aluminum complex can be prepared as either an isolated composition prior to introduction of the zirconium moeity in solvent solution or prepared in situ with zirconium oxychloride, the preferred route being preparation of the stabilized aluminum complex as a separate, isolated composition wherein the aluminum complex solution is dried to remove water and other solvents, and subsequently redispersed in nonaqueous media. Preferably the dimeric aluminum reactant is dissolved in methanol, whereupon propylene glycol is added and the mixture refluxed at 65°–70° C. for one hour to form the stabilized dimeric aluminum complex.

Complexation with —OC(R$_2$)O—, the organofunctional ligand, can be achieved either upon introduction of the ligand to a solution containing only zirconium oxychloride, or after the introduction and reaction of the zirconium oxychloride with the aforementioned stabilized aluminum chlorohydrate. Said reaction shall employ a mole ratio of —OC(R$_2$)O— to total metal of 0.05 to 2.00, the most preferred ratio being 0.10 to 0.50. The route elected for synthesis will result in a significant difference in end product composition as characterized by physical and compositional properties with each type of complex useful in particular types of applications.

It is a further teaching of this invention that the basicity of the dimeric aluminum chlorohydrate moeity critically alters both the reactivity of such with the zirconium moeity and the resultant performance of the aluminum zirconium metallo-organic complex end product. It is understood here the basicity is defined in terms of a divalent Al reactant typified by the general formula:

$$Al_2OH_bCl_c$$

wherein b+c=6, basicity is equal to b/6. The basicity can be varied from 0 to 5/6 (0.83) by reaction of the aluminum chlorohydrate with a chloride source exemplified by, but not restricted to, HCl. Preparation of a reduced (less than 5/6) basicity dimeric aluminum chlorohydrate specie with invariant compositions occurs by careful comingling of the hydrochloric acid and aluminum chlorohydrate so as to maintain a constant temperature of 30° C. to 100° C. resulting from the exothermic addition, the preferred temperature being 40° C. to 60° C. It is to be noted that maintenance of the exotherm temperature at less than 30° C. requires an impractically lengthy addition time, whereas an exotherm temperature in excess of 60° C. may result in variant composition. The reduced basicity product can than be reacted with the aforementioned bidentate ligands, —OR$_1$O— and —OCH(R$_3$)COO resulting in the following compositions:

$$Al_2(R_1O_2)_aOH_bCl_c \text{ or } Al_2(OCHC(R_3)COO)_a{}_aOH_bCl_c$$

where 2a+b+c=6. In a typical preferred composition, following the reaction of equimolar quantities of hydrochloric acid and dimeric aluminum chlorohydrate, a=1.00, c=2.00, b=2.00, and basicity is therefore 0.33.

Compositions prepared in accordance with the teachings of the subject invention are characterized as having a slight yellow color which may range from <50 Pt-Co to Gardner 5 in intensity. Such compositions generally are clear immediately after preparation, but may contain as much as 0.5% insolubles which may be allowed to sediment or removed by conventional filtration techniques.

The active product can be isolated by low vacuum ambient temperature solvent removal, thereby resulting in a highly viscous (>10$^6$ cps) gellatinous mass that, upon complete drying, forms a rigid solid which adheres strongly to glass and resists aqueous dissolution.

Another composition of matter of the invention is the reaction product of the aforementioned aluminum zirconium metallo organic complexes having the structure as previously described and finely divided inorganic mineral fillers, pigments and fibers. Thus, from 0.02 to 1.00 phf (parts per hundred filler) of the active product may be chemically reacted with the surface of a particulate in organic material, such materials to include silica, calcium carbonate, alumina trihydrate, aluminum silicates (Kaolin and the like), talc, wollastonite, glass beads, mica or titanium dioxide resulting in an essentially immediate, largely irreversible alteration in the physical and chemical properties of such particles. On the other hand, dispersion of any of the foregoing particulate minerals in an organic medium in the absence of the composition of the present invention results in sharp visoosity increase, particle agglomeration, nonuniform distribution and poor wetting; treatment with the subject aluminum zirconium metallo-organics, either prior to or at the time of introduction of these particulates to the resinous organic medium results in observable improvements in all of these properties. Such improvements afford the use of significantly increased quantities of such mineral particulates while achieving a uniform dispersion of the mineral in the organic matrix. In the specific instance of such particulates being used in a resinous matrix, be it a thermoset thermoplastic or elastomer, the resultant fabricated article manufactured with such surface modified particulates will show an improvement in physical strength properties which is related to the capability of the finished article being able to transfer an applied stress across the resin particulate interface. It is an object of this invention that the interfacial void which characterizes an untreated filler in contact with a resinous matrix is largely eliminated when the mineral surface has been modified with the subject composition due to:

1. Sizeable changes in the particulate surface energy thereby leading to enhancement of the wetting of the treated particulate by the resin; and 2. Chemical bonding which occurs between the two dissimilar phases through the intermediacy of the aluminum zirconium metallo-organic, one end of which is attached to the particulate and the other end of which attaches to the resin. Specifically, the chemical nature of the mineral surface which is initially highly hydrophilic and organophobic is modified resulting in one which is highly hydrophobic and organophilic.

Although discussion has focused upon the reaction between aluminum zirconium metallo-organic agents and inorganic mineral fillers, it is a further object of the invention that such complex agents are useful in the modification of particulate organics wherein the organic has pendant reactive groups, i.e. hydroxy or halogen substituents. Thus, by non-limiting example the subject composition can be employed to alter the surface of a substance such as tetrabromobisphenol A rendering it more readily dispersible in a resinous system and thereby enhance its efficiency as a flame retardant.

While not wishing to be bound by theory, reaction of the aluminum zirconium metallo-organic agent is postulated to occur between the pendant hydroxy or other groups of both aluminum and zirconium metal centers and the filler substrate surface hydroxy groups or surface adsorbed molecules of water. The heretofore described modification of the filler surface can be readily effected by any of the following reaction modes:

(1) Dissolution of the aluminum zirconium metallo-organic agent in a suitable solvent, such solvents to include water, lower alcohols or fatty alcohols, ketones, carboxylic acids and their esters, tetrahydrofuran, dioxane, halogenated (preferably chlorinated) hydrocarbons, such as carbon tetrachloride or methylene chloride, dimethylsulfoxide, mineral oil, toluene, oxylene and similar organic solvents, and subsequent addition of the mineral or organic filler (5-85 wt percent of total slurry) with concomitant mixing (2) Direct addition of the aluminum zirconium metallo-organic agent to a premixed slurry prepared with any of the aforementioned solvents. Such slurries may contain from 5 to 85 wt percent filler.

(3) Direct addition of the aluminum zirconium metallo-organic to the dry filler and high shear agitation such as provided by a Waring Blender to uniformly distribute the treating agent on the filler surface.

(4) Direct addition of the aluminum zirconium metallo organic to the resin with subsequent addition of the filler accompanied by high shear mixing as exemplified by a Waring blender.

Other methods of contacting fillers with the compositions of the present invention will be apparent to those skilled in the art.

Reaction between the filler substrate and the aluminum zirconium metallo-organic agent typically occurs within seconds after contact of the substrate and modifier as effected by low shear mixing (which may include manual agitation) for slurries having an initial viscosity of less than 50,000 cps. An abrupt viscosity reduction to less than 10% of the original viscosity is indicative of the significant change in the surface character of the filler.

The above disclosed inorganic and organic fillers to be used in accordance with the present invention may broadly include particles ranging in size from 0.05 to 500 microns, preferably 0.5 to 50 microns. Where the composition is used with inorganic or organic fibers of filaments, they may also range from about 0.05 to 500 microns (equivalent cylindrical diameter), preferably 0.05 to 50 microns. While some benefit will be obtained from the use of the present aluminum zirconium metallo-organic agents with inorganic or organic fillers of substantially any size, typically the improvement in properties is more substantial and more necessary with the smaller particles.

Another composition of matter which is the subject of this invention is the reaction product of the subject aluminum zirconium metallo-organic agent and glass fibers either as strands in the forming operation or subsequently as woven fiber glass and woven or nonwoven fiber glass mat. The manufacture of fiber glass typically consists of passing the hot glass fibers as they emerge from the forming bushing through an aqueous sizing bath which includes antistatic agents, wetting agents, binders and, of primary importance in this discussion, coupling (or keying) agents. Such agents in the past have been typified by organosilanes and methacrylato chromic chloride. The subject composition has a capacity to chemically react with both the glass fiber and a resin (most commonly epoxy or unsaturated polyester) and highly soluble and stable in aqueous media, and therefore can be introduced as a replacement for either the silane and/or the methacrylato chromic chloride. Such substitution will impart to the fiber glass the reactivity necessary for successful use in fiber glass reinforced composites and also the necessary antistatic properties to facilitate handling during the manufacture of the fiber glass and its subsequent use in a variety of fabrication techniques (to include spray gun, hand lay-up, and other commonly encountered methods of fiber glass use)

It is a further object of this invention that aluminum zirconium metallo-organic complexes wherein $R_2COO-$ has 14 to 36 carbon atoms are useful in imparting a colorless, durable, water repellant finish to both paper, fiberboard, and textile substrates with performance comparable to, or superior to, the commercially available carboxylato ($C_{14}-C_{18}$) chromic chlorides which are deep green in color.

As detailed in the foregoing discussion, treatment of mineral or organic fillers and pigments, in accordance with the teachings of the subject invention, will permit the usage of elevated levels of such fillers in plastic and elastomeric articles without substantial diminution in physical properties of the finished article, with advantageous reductions in filled resin viscosity, and with attendant cost savings and property benefits. Also, similar treatment of mineral fibers (especially glass fibers), and also carbon fibers will enhance performance of such in glass reinforced matrices.

Additionally, the use of such treated fillers and pigments will permit the use of higher filler levels in paints, coatings, binders, sealants and paper manufacture while maintaining product performance. Moreover, the infinite solubility and long term stability of the subject compositions in aqueous media and the rapid reaction with fillers or pigments at ambient temperature (60° to 100° F.) provides the manufacturers of such products with the opportunity to treat the fillers and pigments they use in situ without altering their manufacturing process or the option of using a pretreated filler with comparable performance advantages.

EXAMPLE 1

Preparation of Sec-Propanolato Aluminum Chlorohydrate Solid

Aluminum chlorohydrate, 0.197 moles Al (21.38 g, 5/6 basic) is dissolved in an equal part of water. The solution is brought to reflux, whereupon a methanolic solution of propylene glycol, 0.0985 moles (7.49 g), is fed to the reactor and reflux maintained subsequent to the addition for ½ hour. The reaction product solution is placed in a drying oven at 110° C.-120° C. for one hour to remove solvent. The dried powder remaining is sec-propanolato aluminum chlorohydrate, ½ basicity.

This is indicated in the IR section shown in FIG. 1. The spectrum of propylene glycol (neat, dotted line in FIG. 1) shows three strong absorbance bands in the 1200-1360 $cm_{-1}$ region at 1230 $cm^{-1}$, 1290 $cm^{-1}$, and 1330 $cm^{-1}$. The latter two bands can be assigned with reasonable certainty to O—H bending vibration modes in the glycol. Upon complexation the O—H bond is destroyed resulting in the disappearance of such bands as clearly revealed in the spectrum of the propanolato aluminum (solid line in FIG. 1). Moreover, the C—O stretching vibrations and related overtone bands found at 840-1230 $cm^{-1}$ have either disappeared or shifted, as seen in the complex spectrum (solid trace).

EXAMPLE 2

Preparation of Carboxylato Functional Aluminum Zirconium Metallo Organic Complex Zirconium oxychloride powder, (44.8% Zr) 0.0329 moles Zr (6 85 g), is combined with 60.00 g of isopropyl alcohol, 30.00 g of acetone, and 4.00 g of concentrated hydrochloride acid.

An alcoholic solution of the reaction product of Example 1 is prepared by dissolving a 27.92 g portion of sec-propanolato aluminum chlorohydrate, 0.197 moles Al in 35.009 of methanol.

The zirconium oxychloride solution as described is heated to 45° C.-60° C. whereupon the solution of sec-propanolato aluminum chlorohydrate is added. The mix formed thereby is heated to reflux and such temperature is maintained for one hour.

Figure 4:
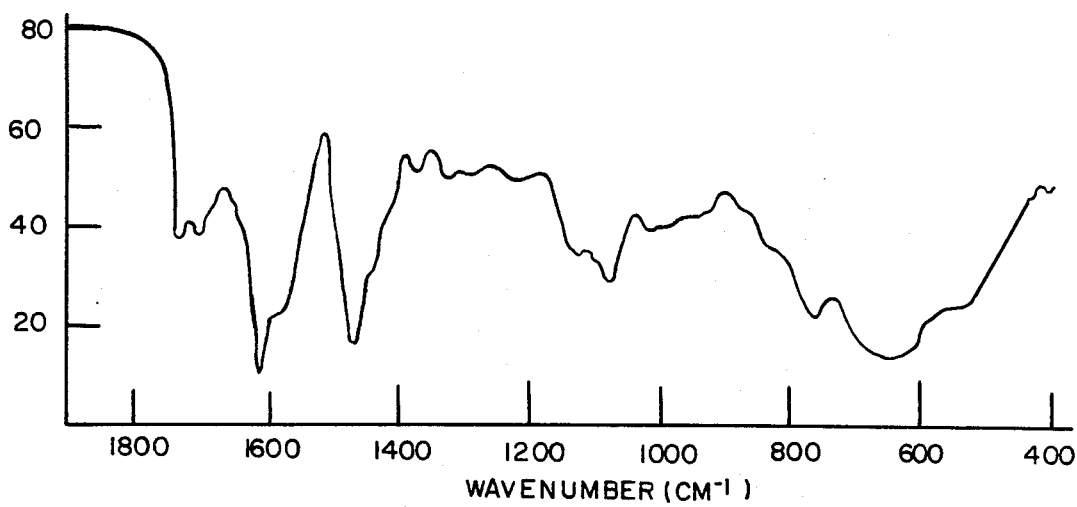
FIG. 4 is the IR scan of the product of Example II, infra.

Thereupon, 0.0823 moles (12.009 g) of adipic acid is added and reflux continued until complexation is complete as determined by infrared spectroscopy (FIG. 4). The product thus prepared has the following characteristics: Specific Gravity (g/ml)—0.937, Flash Point (°F.)—67, Decomposition Point (°C.)—>300, Active Matter (wt %)—22.7, pH (2% Solution)—3.80, Aluminum (wt %)—2.65, Zirconium (wt %)—1.55, Water (wt %)—1.28.

Infrared spectroscopy indicates the product thus prepared to be a hybrid complex wherein one carboxy group of adipic acid forms a complex bridge between the aluminum and zirconium metal centers and the other carboxy group remains uncomplexed. Adipic acid, like most carboxylic acids, is characterized by a strong band at 1700 $cm^{-1}$ representing the —C═O functionality. Upon complexation, the pi bond becomes delocalized over the 3 atom carboxy system O—C—O resulting in a weakened C—O bond which is observed as a downfield shift. Hence, in the subject composition, (FIG. 4) the product is observed to have complex bands at 1585 $cm^{-1}$(sZ), 1610 $cm^{-1}$(s). Furthermore, one —COOH of the dibasic acid remains uncomplexed as indicated by the residual bands at 1700 $cm^{-1}$ and 1735 $cm^{-1}$.

Reaction of adipic acid with only the complex aluminum moiety (FIG. 3) results in a spectrum having only one complex peak at 1615 $cm^{-1}$ (and free —COOH at 1695 cml). In like fashion, reaction of the adipic acid with only the zirconium oxychloride moiety (FIG. 2) results in a water insoluble product having complex peaks at 1540 and 1564 $cm^{-1}$ and loosely bound —COOH at 1735 $cm^{-1}$. The spectrum and related solubility properties suggest that the zirconium complex form may be a salt analogous to sodium adipate.

It is thus believed that the product composition having complex peaks at 1585 $cm^{-1}$ and 1610 $cm^{-1}$ is a hybrid structure in which the bidentate organofunctional ligand is bound to both a zirconium and aluminum atom.

By similar reasoning and spectral interpretation, Examples 3, 4, 5 are observed to have a comparable structure whereby the organofunctional ligand $R_2COO$ is bound to both a zirconium and aluminum atom.

EXAMPLE 3

Preparation of Carboxylato Functional Aluminum (Reduced Basicity) Zirconium Metallo-Organic Complex Zirconium oxychloride powder, (44.8% Zr) 0.0376 moles Zr (7.79 g), is combined with 68.27 g of isopropyl alcohol, 34.14 g of acetone, and 4.55 g of concentrated hydrochloric acid.

An alcoholic solution of the reaction product of Example 1 is prepared by dissolving a 27.96 g portion of the sec-propanolato aluminum chlorohydrate (½ basic), 0.225 moles Al, in 28.63 g of methanol. Subsequent to complete dissolution, concentrated hydrochloric acid, 11.10 g, is slowly added to the reactor with agitation. The rate of addition is controlled so as to prevent the reaction exotherm from exceeding 50° C. The aluminum intermediate formed thereby is ⅓ basic.

The zirconium oxychloride solution as described is heated to 45° C. to 60° C. whereupon the aforementioned reduced basicity (⅓ basic) sec-propanolato aluminum chlorohydrate solution is added. The reaction mixture is then heated to reflux and maintained at that temperature for one hour.

Figure 5:
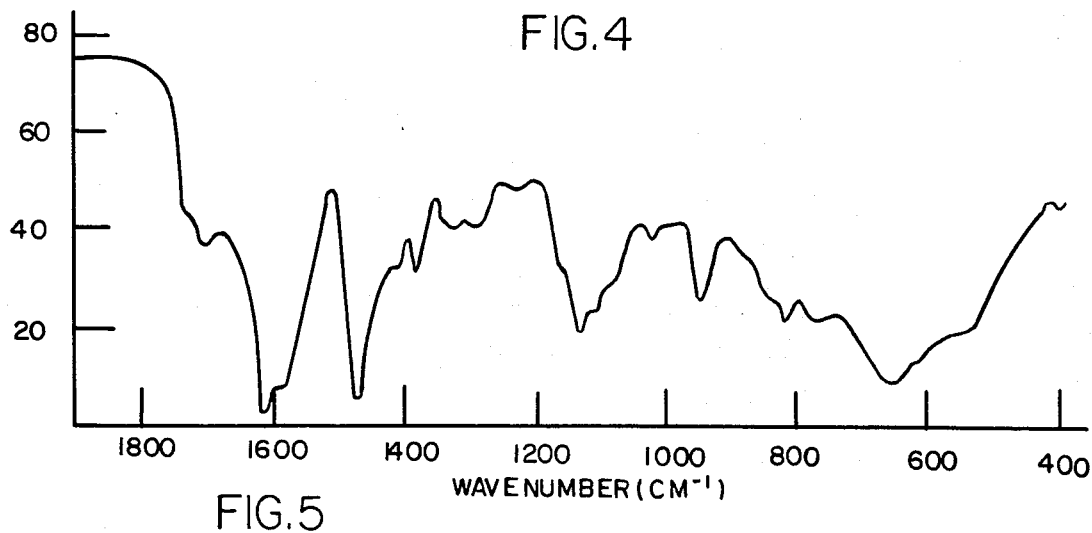
FIG. 5 is the IR scan of the product of Example III, infra.

Thereupon, adipic acid, 0.0935 moles (13.66 g) is added and reflux continued until complexation is complete as determined by infrared spectroscopy, as shown in FIG. 5.

Infrared spectroscopy indicates the product thus prepared to be a hybrid complex wherein one carboxy group of adipic acid forms a complex bridge between the aluminum and zirconium metal centers and the other carboxy group remains uncomplexed.

The product thus prepared has the following characteristics: Specific Gravity (g/ml)—0.974, Flash Point (°F.)—67, Decomposition Point (°C.)—>300, Active Matter (wt %)—24.1, pH (2% Solution)—4.20, Aluminum (wt %)—2.65, Zirconium (wt %) 1.55—Water (wt %)—5.00.

EXAMPLE 4

Preparation of $C_{12}$-$C_{18}$ Functional Aluminum Zirconium Metallo Organic Complex Zirconium oxychloride powder, (44.8% Zr) 0.0329 moles Zr (6.85 g), is combined with 60.00 g of isopropyl alcohol, 30.00 g of acetone, and 4.00 g of concentrated hydrochloric acid.

An alcoholic solution of the reaction product of Example 1 is prepared by dissolving a 27.929 portion of the sec-propanolato aluminum chlorohydrate, 0.197 moles Al, in 35.00 g of methanol.

The zirconium oxychloride solution as described is heated to 45° C.-60° C. whereupon the solution of sec-propanolato aluminum chlorohydrate is added. The mix formed thereby is heated to reflux and such temperature is maintained for one hour.

Figure 6:
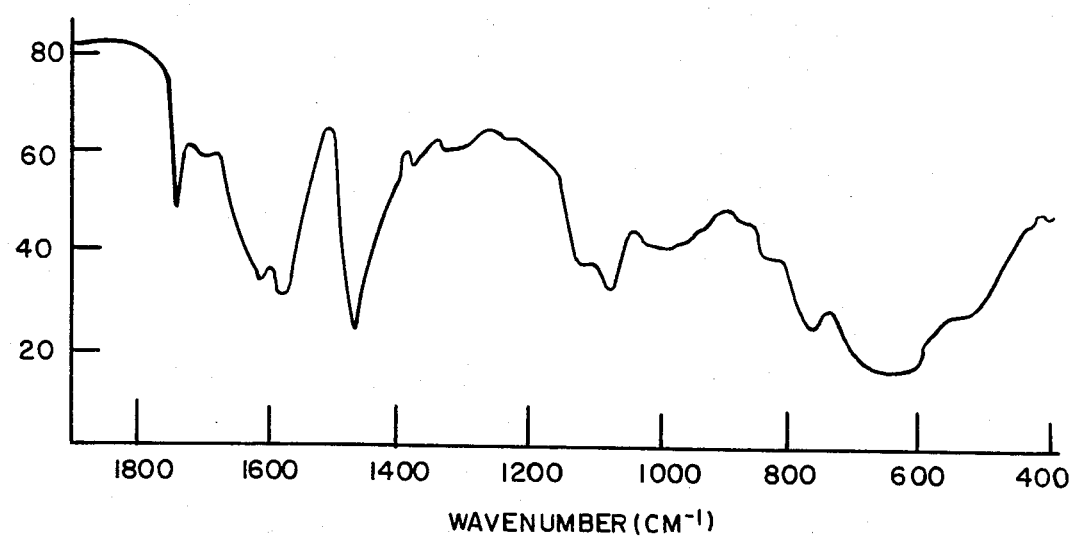
FIG. 6 is the IR scan of the product of Example IV, infra.

Thereupon, a blend of fatty acids, consisting of 90% $C_{14}$, 10% $C_{12}$ and $C_{16}$, of 0.0822 moles (18.74 g), is added and reflux continued until complexation is at least 70% complete as determined by infrared spectroscopy (FIG. 6).

Infrared spectroscopy indicates the product thus prepared to be composed of 70% of a hybrid complex wherein the fatty acids form a complex bridge between the aluminum and zirconium metal centers and the remaining 30% is weakly complexed (1740 cm$^{-1}$).

The product thus prepared has the following characteristics: Specific Gravity (g/ml)—0.923, Flash Point (° F.)—67, Decomposition Point (° C.)—>300, Active Matter (wt %) —25.7, pH (2% Solution)—4.50, Aluminum (wt %)—2.65, Zirconium (wt %)—1.55, Water (wt %)—1.28.

EXAMPLE 5

Preparation Of $C_{12}$–$C_{18}$, Methacrylato Mixed Functional Aluminum Zirconium Metallo Organic Complex Zirconium oxychloride powder, (44.8% Zr) 0.0329 moles Zr (6.85 g), is combined with 60.00 g of isopropyl alcohol, 30.00 g of acetone, and 4.00 g of concentrated hydrochloric acid. Methacrylic acid, 0.0655 moles (5.64 g ), is added to the mixture with agitation at ambient temperature. The mixture is heated to reflux temperature and held for 0.5 to 1.0 hours.

An alcoholic solution of the reaction product of Example 1 is prepared by dissolving sec-propanolato aluminum chlorohydrate, 0.197 moles Al (27.92 g ) in 50.00 g of methanol. The reaction mixture described above is cooled to 45° C. whereupon the solution of sec-propanolato aluminum chlorohydrate is added. The resultant aluminum zirconium methacrylato mixture is reheated to reflux for 0.5 to 1.5 hours.

Figure 7:
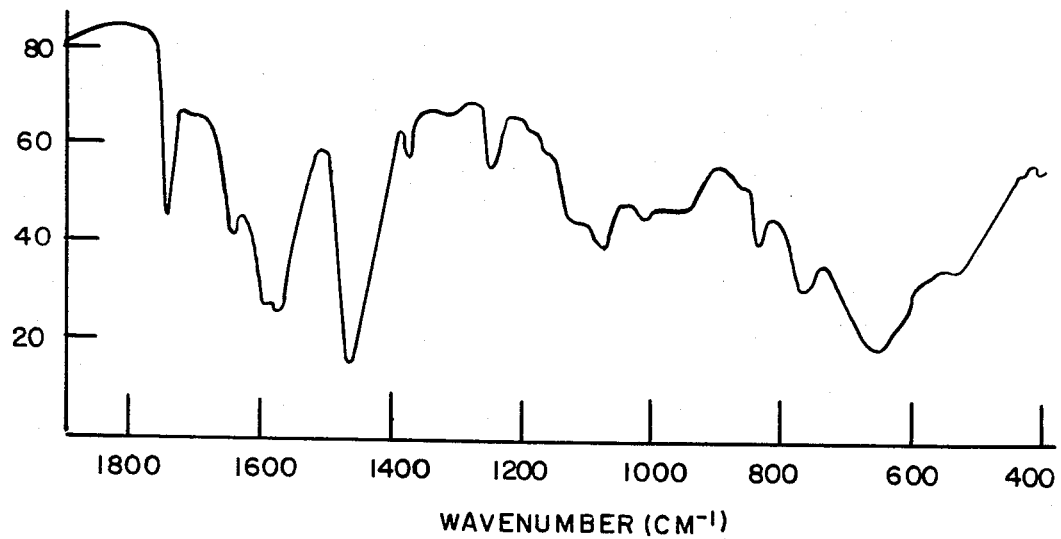
FIG. 7 is the IR scan of the product of Example V, infra.

The aluminum zirconium methacrylato product is cooled to 60° C. whereupon a blend of fatty acids, consisting of 90% $C_{14}$, 10% $C_{12}$ and $C_{16}$, 0.0822 moles (18.74 g), is added and reflux continued until complexation is at least 70% complete as determined by infrared spectroscopy (FIG. 7).

Infrared spectroscopy indicates the product thus prepared to be a compound of a hybrid complex wherein the 70% of the fatty acids and 100% of the methacrylic acid form a complex bridge between aluminum and zirconium metal centers.

The product thus prepared has the following characteristics: Specific Gravity (g/ml)—0.910, Flash Point (° F.)—67, Decomposition Point (° C.)—>300, Active Matter (wt %) —24.0, pH (2% Solution)—3.70, Aluminum (wt %)—2.63, Zirconium (wt %)—1.51, Water (wt %)—1.26.

EXAMPLE 6

Treatment Of Inorganic Mineral Fillers With Aluminum Zirconium Metallo Organic Surface Modifiers This example teaches the use of compositions of this invention for the surface modification of finely divided inorganic mineral fillers characterized by particle sizes between 0.5 and 5.0 microns. Thus, filler dispersions were prepared as shown in the accompanying table at the indicated concentrations and in the indicated solvents. For example, 400 g of alumina trihydrate (1 micron particle size) is dispersed in 600 g of deionized water using a 4 blade high speed paint agitator. To a 150 g sample of the dispersion containing 60 g of alumina trihydrate having a viscosity of 19800 cps (Brookfield, Spindle 5, 20 rpm) is added 0.9 g (1.5 phf) of the composition of Example 3 (0.34 phf of active matter). The slurry is agitated manually for 30 seconds at 20° C. whereupon the viscosity is determined to have decreased to 500 cps (Brookfield, Spindle 5, 20 rpm). Seven days later the viscosity of the treated slurry has undergone further viscosity reduction to <50 cps, hence suggestive of the irreversibility of surface modification (Table I).

Alternatively, the composition of Example 5, 0.9 g (1.5 phf, 0.34 phf of active matter) may be dissolved in 90 g of deionized water. Alumina trihydrate, 60 g , is added to the aqueous mix whereupon a slurry having a viscosity of 100 cps results (Brookfield, Spindle 5, 20 rpm).

It is abundantly documented (Table I) that surface modification of the indicated mineral fillers with the compositions of Examples 2, 3, 4, 5 result in pronounced and irreversible reductions in filler slurry viscosity in excess of 98 percent. It is further noted that the addition sequence by which a slurry is prepared can markedly affect the observed viscosity. Such is the case with calcium carbonate in alcohol where addition to the slurry is marginally effective (17.5% viscosity reduction after 7 days) as contrasted with prior dissolution of the surface modifier in solvent which results in >99% reduction in viscosity.

Examination of the data pertaining to TiO$_2$ (Table I) is indicative of the preferred use of a specific composition with a given filler due to significant differences in surface modifier performance.

TABLE I

| FILLER | SOLVENT | SLURRY CONC WT % | Al—Zr SURFACE MODIFIER phf, ACTIVE MATTER | Al—Zr SURFACE MODIFIER EXAMPLE NUMBER | ADD'N MODE | VISCOSITY, cps | | |
|---|---|---|---|---|---|---|---|---|
| | | | | | | U/T | INITIAL TREATED | 7 DAYS TREATED |
| Alumina Tri-hydrate (1 micron) | Water | 40 | 0.34 | III | Slurry[1] | 19800 | 500 | <50 |
| | | | 0.34 | | Solvent[2] | 12500 | 100 | 100 |
| | Alcohol | 40 | 0.23 | V | Slurry | 20000 | <100 | <100 |
| Calcium Carbonate (1 micron) | Alcohol | 70 | 0.34 | III | Slurry | 20000 | 34000 | 16500 |
| | | | 0.34 | | Solvent | 39280 | 500 | 250 |
| Silica (1.8 micron) | Water | 70 | 0.46 | V | Slurry | 16000 | <100 | |
| | Alcohol | 70 | 0.03 | II | Slurry | 49000 | 200 | 100 |
| | | | 0.03 | | Solvent | 26250 | 200 | 100 |
| Clay | Alcohol | 60 | 0.34 | II | Slurry | 16000 | 2000 | 250 |

TABLE I-continued

| FILLER | SOLVENT | SLURRY CONC WT % | Al—Zr SURFACE MODIFIER phf, ACTIVE MATTER | Al—Zr SURFACE MODIFIER EXAMPLE NUMBER | ADD'N MODE | VISCOSITY, cps | | |
|---|---|---|---|---|---|---|---|---|
| | | | | | | U/T | INITIAL TREATED | 7 DAYS TREATED |
| (4 micron) | | | 0.34 | | Solvent | 18250 | <50 | 250 |
| Titanium | Water | 70 | 0.24 | V | Slurry | 50000+ | 750 | 500 |
| Dioxide | | | 0.30 | | Solvent | 50000+ | 1000 | 850 |
| (0.5 micron) | Alcohol | 70 | 0.50 | V | Slurry | 50000+ | 500 | 500 |
| | Water | 70 | 0.24 | II | Slurry | 50000+ | 500 | 1500 |
| | Alcohol | 70 | 0.24 | II | Slurry | 50000 | 250 | <100 |

[1]Surface modifier added to filler slurry.
[2]Surface modifier dispersed in solvent, filler added.

EXAMPLES 7-21
Other Aluminum/Zirconium Metallo Organic Agents

In a manner similar to that detailed for Examples 1 through 6, other aluminum zirconium metallo-organic complex agents were prepared having the substituents and ratios of substituents indicated in Table II below.

TABLE II

| | $R_3CH_2(OH)COOH$ or $-OR_1O-$ | $R_2COOH$ | MOLES Al:Zr | BASICITY DIMERIC ALUMINUM |
|---|---|---|---|---|
| Example 7 | $-OCH(CH_3)CH_2-O-$ | $CH_2=C(CH_3)COOH$ | 6:1 | 0.50 |
| Example 8 | $-OCH(CH_3)CH_2-O-$ | $CH_2=C(CH_3)COOH$ | 9:1 | 0.50 |
| Example 9 | $-OCH(CH_3)CH_2-O-$ | $NH_2-CH_2CH_2COOH$ | 9:1 | 0.50 |
| Example 10 | $-OCH(CH_3)CH_2O-$ | HOOCCOOH | 6:1 | 0.50 |
| Example 11 | $-OCH(CH_3)CH_2O-$ | $HOOC(CH_2)COOH$ | 6:1 | 0.50 |
| Example 12 | $-OCH(CH_3)CH_2O-$ | $HOOC(CH_2)_2COOH$ | 6:1 | 0.50 |
| Example 13 | $-OCH(CH_3)CH_2O-$ | $HOOC(CH_2)_3COOH$ | 6:1 | 0.50 |
| Example 14 | $-OCH(CH_3)CH_2O-$ | $HOOC(CH_2)_4COOH$ | 6:1 | 0.50 |
| Example 15 | $-OCH(CH_3)CH_2O-$ | HOOCCOOH | 6:1 | 0.33 |
| Example 16 | $-OCH(CH_3)CH_2O-$ | $HOOC(CH_2)COOH$ | 6:1 | 0.33 |
| Example 17 | $-OCH(CH_3)CH_2)O-$ | $HOOC(CH_2)_2COOH$ | 6:1 | 0.33 |
| Example 18 | $-OCH(CH_3)CH_2O-$ | $HOOC(CH_2)_3COOH$ | 6:1 | 0.33 |
| Example 19 | $-OCH(CH_3)CH_2O-$ | $HOOC(CH_2)_4COOH$ | 6:1 | 0.33 |
| Example 20 | $HO-CH_2COOH$ | $CH_2=C(CH_3)COOH$ | 6:1 | 0.50 |
| Example 21 | $HO-CH_2COOH$ | $CH_2=C(CH_3)COOH$ | 6:1 | 0.33 |

All of the compositions provide aluminum zirconium metallo-organic treatment agents which were useful in improving the surface properties of inorganic fillers and like materials. It is also possible to obtain useful compositions using other organic reactants and other Al:Zr ratios and basicities, outside the range indicated in Table II, but such products should be checked for stability and effectiveness before use. Preferably, the compositions made in accordance with the present invention have shelf life of at least 30 days.

EXAMPLE 22
Preparation And Use Of Inorganic Mineral Filler Pretreated With Aluminum Zirconium Organic Surface Modifiers A 70 wt % alcoholic dispersion of silica (1.8 micron praticle size) is prepared as per the procedure described in Example 6. To the slurry is added 0.03 phf (active matter) of an aluminum zirconium metallo organic surface modifying agent, made in accordance with the procedure of Example 2 having the composition of Example 12. The viscosity of the untreated and treated slurry is noted (as shown in Table III). The slurry is then placed in a drying oven at 110° C. for 30 minutes to remove solvent whereupon to the dry treated silica is added an amount of alcohol equivalent to that which is removed during the drying process. The silica is redispersed and the viscosity is measured and observed to be equivalent to the analogous slurry prior to drying. The results are shown in Table III.

TABLE III

| PROCESS DESCRIPTION | SOLVENT | Al—Zr SURFACE MODIFIER phf, ACTIVE MATTER | VISCOSITY cps |
|---|---|---|---|
| 1. Untreated Silica Slurry | Alcohol | — | 9000 |
| 2. Treated Silica Slurry | Alcohol | 0.03 | <100 |
| 3. Dry Silica | Alcohol | — | — |
| 4. Redispersed Treated Silica | Alcohol | — | <100 |

Similarly, a 40 wt % alcoholic dispersion of alumina trihydrate (1 micron particle size) is prepared, treated with 0.34 phf (active matter) of an aluminum zirconium metallo-organic surface modifier and then processed as described in the foregoing silica dispersion system. The results (Table IV) show a 90% viscosity reduction upon adding the surface modifier and >99.5% viscosity reduction upon drying and redispersion.

TABLE IV

| PROCESS DESCRIPTION | SOLVENT | Al—Zr SURFACE MODIFIER phf, ACTIVE MATTER | VISCOSITY cps |
|---|---|---|---|
| 1. Untreated Alumina Trihydrate Slurry | Alcohol | — | 50000+ |
| 2. Treated Alumina Trihydrate Slurry | Alcohol | 0.34 | 5000 |
| 3. Dry Alumina Trihydrate | — | — | — |
| 4. Redispersed Alumina | Alcohol | 0.34 | <100 |

TABLE IV-continued

| PROCESS DESCRIPTION | SOLVENT | Al—Zr SURFACE MODIFIER phf, ACTIVE MATTER | VISCOSITY cps |
|---|---|---|---|
| Trihydrate | | | |

EXAMPLE 23

Improvements In Performance Of Surface Treated Glass Reinforced Polyester Panels A 2 wt percent aqueous bath of the composition of Example II is prepared having a pH of 3.7. Heat cleaned woven fiber glass mat is soaked in the aqueous bath, the excess moisture removed, and the fabric dried at 105° C. for 15 minutes. A wet pick up of 34% and a dry pick up of 0.13% is determined.

The fabric is separated into one inch lengths of roving which is further heated for 30 minutes at 105° C. Thereupon, the shredded fabric is admixed with an unsaturated polyester resin mixture consisting of Reichhold Polylite 31–006, >90%, <10% methyl methacrylate and styrene, and <1% of methyl ethyl ketone peroxide.

The glass filled resin is cured for 30 minutes at 10,000 psi and 112° C. The transparent finished glass reinforced panel is then exposed to steam for 6 hours resulting in some interfacial delamination at the glass resin interface as manifested by the appearance of glass strands, thus imparting opacity.

It is known to those skilled in the art that the degree of fiber prominence after steam exposure is directly proportional to wet flexural strength. The panel prepared using the glass treated with the composition of the invention is characterized by an average of 10 fibers/sq in (largely transparent), whereas a panel prepared with untreated glass is virtually opaque, having >>100 fibers/sq in.

EXAMPLE 24

Surface Treatment Of Paper Substrates To Impart Durable Water Repellancy

A 5 wt % aqueous bath of Example IV is prepared. A 3"×6" section of unbleached kraft paper is saturated in the solution, padded, and dried at 100° C. for 2 minutes.

Similarly, two 3"×6" sections of unbleached kraft paper are saturated in 5% solutions of DuPont Quilon C and L (a commercially used water repellant), padded, and dried at 110° C. for 2 minutes.

One drop of deionized water is carefully placed on the flattened surface of each of the above sheets and also on the untreated kraft stock. In the latter instance, the water is observed to penetrate upon contact. In contrast, after 24 h. there is no indication of surface wetting on the sheets treated with either the aluminum zirconium metallo-organic or the Quilon C or L. Additionally, whereas the Quilon products impart a distinctly green color to the substrate, treatment with the aluminum zirconium metallo-organic results in no apparent discoloration.

In like fashion, textile substrates may be treated with the composition of Example IV achieving similar water repellancy without undesirable impact on aesthetics.

While the exemplary embodiments have been disclosed with particularity, other embodiments will be readily apparent to those skilled in the art from consideration of the present disclosure, or from practice of the invention disclosed herein. The embodiments discussed are to be considered as exemplary only, and the true scope of the invention should be determined by a consideration of the appended claims.

We claim:

1. A composition of matter comprising the reaction product of a chelated aluminum moiety, an organofunctional ligand and a zirconium oxyhalide, the organofunctional ligand being complexed with and chemically bound to the chelated aluminum moiety and the zirconium moiety, the aluminum moiety having the formula:

$$Al_2(OR_1O)_a A_b B_c$$

wherein A or B is hydroxy or halogen and a, b and c are numerical values such that $2a+b+c=6$, and $(OR_1O)$ is (a) an alpha, beta or alpha, gamma glycol group in which $R_1$ is an alkyl group having 1 to 6 carbon atoms or (b) an alpha-hydroxy carboxylic acid residue having the formula:

$$-O-\underset{\underset{H}{|}}{C}H-\underset{\underset{}{\overset{O}{\|}}}{C}-O-$$

wherein $R_3$ is H or an alkyl group having from 1 to 4 carbon atoms; the organofunctional ligand is (1) an alkyl, alkenyl, alkynl or aralkyl carboxylic acid having from 2 to 36 carbon atoms, (2) an aminofunctional carboxylic acid having from 2 to 18 carbon atoms, (3) a dibasic carboxylic acid having from 2 to 18 carbon atoms, (4) an acid anhydride of a dibasic acid having from 2 to 18 carbon atoms, (4) an acid anhydride of a dibasic acid having from 2 to 18 carbon atoms, (5) a mercapto functional oarboxylic acid having from 2 to 18 carbon atoms, or (6) an epoxy functional carboxylic acid having from 2 to 18 carbon atoms; and the zirconium oxyhalide moiety has the formula:

$$ZrA_d B_e$$

wherein A and B are as above-defined and d and e are numerical values such that $d+e=4$; the molar ratio of chelated aluminum moiety to zirconium oxyhalide moiety being from about 1.5 to 10, and the molar ratio of organofunctional ligand to total metal being from about 0.05 to 2.

2. The composition of matter of claim 1, wherein said composition is soluble in alcohols, ketones, carboxylic acids, carboxylic acid esters, tetrahydrofurane, dioxane, dimethylformamide, dimethylsulfone, dimethylacetamide, a halogenated hydrocarbon, mineral oil, xylene or toluene.

3. The composition of claim 1, wherein $R_1$ is an alkyl group of 2 or 3 carbon atoms or $$-\underset{\underset{H}{|}}{C}H-\underset{\underset{}{\overset{O}{\|}}}{C}-$$

and $R_3$ is H or $CH_3$.

4. The composition of claim 1, wherein the reaction product corresponds to the empirical formula:

$$(Al_2(OR_1O)_a A_b B_c)_x(OC(R_2)O)_y(ZrA_d B_e)_z$$

wherein X, Y, and Z are at least 1, $R_2$ is an alkyl, alkenyl, aminoalkyl, carboxyalkyl, mercaptoalkyl, or epoxyalkyl group, having from 2 to 17 carbon atoms, and the ratio of X:Z is from about 2:1 to about 5:1.

5. The composition of claim 4, wherein the ratio of Y:2X+Z is from about 0.1 to about 1.0.

6. The composition of claim 4, wherein $R_1$ is alkyl of 2 or 3 carbon atoms or

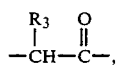

$R_3$ is H or alkyl of 1 to 4 carbon atoms and $R_2$ is alkenyl or 2 to 5 carbon atoms, aminoalkyl of 1 to 5 carbon atoms, an alkyl carboxylic acid having 1 to 18 carbon atoms, or mercaptoalkyl of 2 to 17 carbon atoms.

7. The composition of claim 4, wherein $R_1$ is alpha, beta propyl or methyl acyl and $OC(R_2)O$ is the anion of 2-methyl propanoic acid, propanoic acid, beta alanine, oxalic acid, malonic acid, succinic acid, glutaric acid, adipic acid, or a fatty acid.

8. The composition of claim 4, wherein X:Z is about 3:1, Y:2X+Z is about 0.5, A is hydroxy, B is chlorine, $R_1$ is n-propyl or isopropyl, $R_2COO-$ is methacrylic acid, a is about 1, b is about 3, and c is about 1.

9. The composition of claim 4, wherein X:Z is about 3:1, Y:2X+Z is about 0.35, A is hydroxy, B is chlorine, $R_1$ has three carbon atoms, $R_2$ COO— is methacrylic acid, a is about 1, b is about 3, and c is about 1.

10. The composition of claim 4 wherein X:Z is about 3:1, Y:2X+Z to about 0.35, A is hydroxy, B is chlorine, $R_1$ has 3 carbon atoms, $R_2COO-$ is adipic acid, a is about 1, b is about 2, and c is about 2.

11. The composition of claim 4, wherein X:Z is about 3:1, Y:2X+Z is 0.50, A is hydroxy, B is chlorine, $R_1$ has 3 carbon atoms, $R_2COO-$ consists of a combination of 2 methyl-propenoic acid and $C_{12}$, $C_{14}$ and $C_{16}$ fatty acids, a is about 1, b is about 3, c is about 1.

12. The composition of claim 4, wherein X:Z is about 3.1, Y:2X+Z is about 0.35, A is hydroxy, B is chlorine, $R_1$ is n-propyl,isopropyl, $R_2$ COO— is myristic, palmitic, stearic, or oleic acid, or mixtures thereof.

13. The composition of claim 12, wherein $R_2COO-$ is a mixture of fatty acids containing about 90% myristic acid.

14. A method of preparing a composition of matter useful as a coupling agent, comprising reacting a chelated aluminum moiety with an organofunctional ligand and a zirconium oxyhalide, the aluminum moiety having the formula:

$$Al_2(OR_1O)_a\ A_bB_c$$

wherein A or B is hydroxy or halogen and a, b and c are numerical values such that $2a+b+c=6$, and $(OR_1O)$ is (a) an alpha, beta or alpha, gamma glycol group in which $R_1$ is an alkyl, alkenyl or alkynyl group having 1 to 6 carbon atoms or (b) an alpha-hydroxy carboxylic acid residue having the formula:

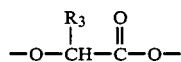

wherein $R_3$ is H or any alkyl group having from 1 to 4 carbon atoms;
the organofunctional ligand is (1) an alkyl, alkenyl, alkynyl or aralkyl carboxylic acid having from 2 to 36 carbon atoms, (2) an aminofunctional carboxylic acid having from 2 to 18 carbon atoms, (3) a dibasic carboxylic acid having from 2 to 18 carbon atoms, (4) an acid anhydride of a dibasic acid having from 2 to 18 carbon atoms, (5) a mercapto functional carboxylic acid having from 2 to 18 carbon atoms, or (6) an epoxy functional carboxylic acid having from 2 to 18 carbon atoms; and the zirconium oxyhalide moiety has the formula:

$$ZrA_dB_e$$

wherein A and B are as above-defined and d and e are numerical values such that $d+e=4$; the molar ratio of chelated aluminum moiety to zirconium oxyhalide moiety being from about 1.5 to 10, and the molar ratio of organofunctional ligand to total metal being from about 0.05 to 2, and the reaction being carried out in an organic solvent containing less than about five percent by weight water.

15. The method of claim 14, wherein the reaction is carried out in a solvent comprising an alkyl alcohol having from 1 to 12 carbon atoms, an alkyl ketone having from 1 to 6 carbon atoms, or mixtures thereof.

16. The method of claim 15, wherein $R_1$ is alkyl of 2 or 3 carbon atoms or

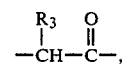

and $R_3$ is H or $CH_3$.

17. The method of claim 15, wherein the reaction product corresponds to the empirical formula:

$$[AL_2(OR_1O)_aA\ _bB_c]_x[OC(R_2)O]_y[ZrA_dB_e]_z$$

wherein X, Y, and Z are at least 1, $R_2$ is an alkyl, aralkyl, alkenyl, alkynyl, aminoalkyl, carboxyalkyl, mercaptoalkyl, or epoxyalkyl group, having from 1 to 17 carbon atoms, and the ratio of X:Z is from about 2:1 to about 5:1.

18. The method of claim 15, wherein the ratio of Y:2X+Z is from about 0.1 to about 1.0, $R_1$ is alkyl of 2 or 3 carbon atoms or

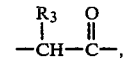

$R_3$ is H or alkyl of 1 to 4 carbon atoms, and $R_2$ is 2-methyl propenoic acid, propenoic acid, beta-alanine, oxalic acid, malonic acid, succinic acid, glutaric acid or adipic acid.

19. The method of claim 15, further comprising forming the aluminum halohydrate chelate complex by reacting an aluminum halohydrate with a bidentate chelating agent having the formula $HOR_1OH$, wherein $R_1$ is an alkyl, alkenyl or alkynyl group having from 1 to 6 carbon atoms, or

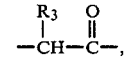

where $R_3$ is H or an alkyl group having from 1 to 4 carbon atoms.

20. The method of claim 19, where the aluminum halohydrate is aluminum chlorohydrate, having a basicity of from 0 to 0.83.

21. The method of claim 19, where the chelated aluminum moiety, organofunctional ligand and zirconium oxyhalide are reacted in a solvent which is a mixture of an alkyl alcohol having from 1 to 3 carbon atoms, and an alkyl ketone having from 1 to 3 carbon atoms, the final concentration of coupling agent in the solvent being from about 15 to 50 percent.

22. A composition comprising the product of admixture of:

(I) the reaction product of a chelated aluminum moiety, an organofunctional ligand and a zirconium oxyhalide, the organofunctional ligand being complexed with and chemically bound to the chelated aluminum moiety and the zirconium moiety, the aluminum moiety having the formula:

$$Al_2(OR_1O)_a A_b B_c$$

wherein A or B can be hydroxy or halogen and a, b and c are numerical values such that $2a+b+c=6$, and $(OR_1O)$ is (a) an alpha, beta or alpha, gamma glycol group in which $R_1$ is an alkyl, alkenyl or alkynyl group having 1 to 6 carbon atoms or (b) an alpha-hydroxy carboxylic acid residue having the formula:

$$-O-\underset{\underset{R_3}{|}}{C}H-\overset{\overset{O}{\|}}{C}-O$$

wherein $R_3$ is H or an alkyl group having from 1 to 4 carbon atoms; the organofunctional ligand is (1) an alkyl, alkenyl, alkynyl, or aralkyl carboxylic acid having from 2 to 36 carbon atoms, (2) an aminofunctional carboxylic acid having from 2 to 18 carbon atoms, (3) a dibasic carboxylic acid having from 2 to 18 carbon atoms, (4) an acid anhydride of a dibasic acid having from 2 to 18 carbon atoms, (5) a mercapto functional carboxylic aid having from 2 to 18 carbon atoms, or (6) an epoxy functional carboxylic acid having from 2 to 18 carbon atoms; and the zirconium oxyhalide moiety has the formula:

$$ZrA_d B_e$$

wherein A and B are as above-defined and d and e are numerical values such that $d+e=4$; the molar ratio of chelated aluminum moiety to zirconium oxyhalide moiety being from about 1.5 to 10, and the molar ratio of organofunctional ligand to total metal being from about 0.05 to 2, said reaction product being formed in the substantial absence of water, and (II) a substrate, said substrate being:
(a) filler selected from the group of glass, silica, calcium carbonate, alumina trihydrate, aluminum silicate, talc, wollastonite, mica, titanium dioxide, and an organic particulate having reactive groups:
(b) paper;
(c) fiberboard;
(d) textile; or
(e) mixtures thereof.

23. The composition of claim 22, wherein the inorganic filler comprises glass fibers said composition having been formed in an organic solvent in the substantial absence of water.

24. A composite product, comprising the composition of claim 22 and a resin selected from the group of thermoset, thermoplastic and elastomeric resins.

* * * * *